United States Patent [19]  [11] 4,053,595
Zeck et al.  [45] Oct. 11, 1977

[54] SYNERGISTIC COMPOSITION FOR THE CONTROL OF INSECTS

[75] Inventors: Walter Maria Zeck; August Cesar deMarshall; André Prosper Wybou, all of Vero Beach, Fla.

[73] Assignees: Mobay Chemical Corporation, Pittsburgh, Pa.; Bayer Aktiengesellschaft, Leverkusen, Germany

[21] Appl. No.: 639,957

[22] Filed: Dec. 11, 1975

[51] Int. Cl.$^2$ .......................... A01N 9/02; A01N 9/20; A01N 9/36
[52] U.S. Cl. ..................................... 424/216; 424/326
[58] Field of Search ................................ 424/216, 326

[56] References Cited

U.S. PATENT DOCUMENTS 3,502,720  3/1970  Unna et al. ..................... 424/326 X
3,825,636  7/1974  Kishino et al. ................. 424/210 X Primary Examiner—Allen J. Robinson
Attorney, Agent, or Firm—Burgess, Dinklage & Sprung

[57] ABSTRACT

Insecticidal compositions in the form of synergistic combinations of O-ethyl-O-[4-(methylthio)phenyl]-S-propyl phosphorodithioate and N'-(4-chloro-a-tolyl)-N,N-dimethylformamidine which are individually known compounds, which combinations possess synergistic insecticidal properties especially for the control of insects which infest cotton.

9 Claims, No Drawings

SYNERGISTIC COMPOSITION FOR THE CONTROL OF INSECTS

The present invention relates to and has for its objects the provision of particular new insecticidal compositions in the form of synergistic combinations of O-ethyl-O-[4-methyl-thio)phenyl]-S-propyl phosphorodithioate and N'-(4-chloro-o-tolyl)-N,N-dimethylformamidine which are individually known compounds which combinations possess outstanding synergistic insecticidal properties especially for growing cotton optionally in the form of carrier composition mixtures of such synergistic combinations with solid and/or liquid dispersible carrier vehicles, and methods for using such synergistic combinations in a new way especially for combating insects, with other and further objects becoming apparent from a study of the within specification and accompanying examples.

It is taught in U.S. Pat. No. 3,825,636 that compounds such as O-ethyl-O-[4-(methylthio)pheny]-S-propyl phosphorodithioate can be used as insecticides.

It is also known from U.S. Pat. No. 3,502,720 that N'-(4-chloro-o-tolyl)-N,N-dimethylformamidine is suitable for combating insects.

If has now been found that combinations of these wherein the O-ethyl-O-[4-(methylthio)phenyl]-S-propyl phosphorodithioate is present in a weight ratio relative to the N'-(4-chloro-o-tolyl)-N,N-dimethylformamidine of 1 to about 0.125 - 0.5 and preferably 1 to about 0.16 - 0.5 is especially effective in fighting insects and particularly Lepidoptera, especially Heliothis species, which infest crops such as corn, soybeans, tobacco and particularly cotton.

Surprisingly, the insecticidal effectiveness of the particular new synergistic combinations of active compounds according to the present invention is substantially higher than the sum of the separate effects of the individual active compounds. This is not merely a supplementary or additive effect, but rather a genuine synergistic effect which was not to be foreseen. Significantly, this synergistic effect is particularly great when limited to specific ratios of concentration as noted above.

Advantageously, the synergistic combinations of active compounds according to the present invention are markedly superior to known active compounds conventionally used for insect control in agricultural crops. The instant synergistic combinations of active compound therefore represent a valuable contribution to the art of insect control agents.

The compositions can be applied to a variety of insects, both of the biting and sucking type.

To the sucking insects there belong, in the main, aphids (Aphididae) such as the green peach aphid (*Myzus persicae*), the beam aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*), the cotton bollworm (*Heliothis zea*), and the tobacco budworm (*Heliothis virescens*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the boll weevil (*Authonomus grandis*), the raspberry beetle (*Buturus tometosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzae-philus surinamensis*), and also species living in the soil, for example wireworms (Agriotes spec.) and larvae of the cockchafer (*Melolontha melolontha*), cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta;* further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further gnats, for example mosquitoes such as the yellow fever mosquito (*Aedes aegypti*), the northern house mosquito (Culexpinpiens) and the malaria mosquito (*Anopheles stephensi*).

Of these, the invention is especially valuable for use against Lepidoptera and especially of the sub-genus Heliothis, e.g. the cotton boll worm complex (*Heliothis Virescens* and *Zea*) and the cotton leaf perforator (*Bucculatric Thurberiella*). In addition to application to cotton, the composition is also suited for application to corn, soybeans and tobacco.

The active compounds according to the instant invention can be utilized, if desired, in the form of the usual formulations of compositions with conventional inert (i.e., plant compatible or herbicidally inert) pesticide diluents or extenders, i.e., diluents, carriers or extenders of the type usable in conventional pesticide formulations or compositions, e.g., conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g., conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g., benzene, toluene, xylene, alkyl napthalenes, etc.), halogenated, especially chlorinated, aromatic hydrocarbons (e.g., chlorobenzenes, etc.), cycloalkanes, (e.g., cyclohexane, etc.), paraffins (e.g., petroleum or mineral oil fractions), chlorinated aliphatic hydrocarbons (e.g., methylene chloride, chloroethylenes, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, etc.), and/or water; as well as inert dispersible finely divided solid carriers, such as ground natural minerals (e.g., kaolins, clays, alumina, silica, chalk, i.e., calcium carbonate, talc, attapulgite, montmorillonite, kieselguhr, etc.), and ground synthetic minerals (e.g., highly dispersed silicic acid, silicates, e.g., alkali silicates, etc.); whereas the following may be chiefly considered for use as conventional carrier vehicle assistants, e.g., surface-active agents, for this purpose: emulsifying agents, such as non-ionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with such solid and/or liquid dispersible carrier vehicles and/or with other known compatible active agents, especially plant protection agents, such as other insecticides, or acaricides, nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compounds are present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0001-10%, preferably 0.01-1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g., a surfaceactive agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e., by applying such compounds or by applying a liquid composition containing the same, via very effective atomizing equipment, in finely divided form, e.g., average particle diameter of from 50-100 microns, or even less, i.e., mist form, for example by airplane crop spraying techniques. Only up to at most about a few liters-hectare are needed, and often amounts only up to about 0.5 to 1 pound per acre are sufficient. In this process it is possible to use highly concentrated liquid compositions with said liquid carrier vehicles containing from about 20 to about 95% by weight of the active compounds or even the 100% active substances along, e.g., about 20-100% by weight of the active compounds.

Furthermore, the present invention contemplates methods of selectively killing, combating or controlling pests, which comprises applying to at least one of correspondingly (a) such pests and (b) the corresponding habitat thereof, i.e., the locus to be protected, e.g., to a growing crop, to an area where a crop is to be grown or to a domestic animal, a correspondingly combative or toxic amount, i.e., a pesticidally effective amount, of the particular active compounds of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compounds utilized in admixture with the carrier vehicle will depend upon the intended application. Therefore, in special cases it is possible to go above or below the aforementioned concentration ranges.

The unexpected superiority and outstanding activity of the particular compositions of the present invention are illustrated, without limitation, by the following examples:

EXAMPLE 1

*Heliothis Virescens* and *Zea* (cotton boll worm complex)

Solvent: xylene
Emulsifier: alkylaryl polyglycol ether

To produce a suitable preparation of active material, a solution was made up containing 66.2 weight percent of 0-ethyl-O-[4-(methylthio)phenyl]-S-propyl phosphorodithioate (A), 10 weight percent of emulsifier and 23.8 weight percent of solvent. To this solution in some instances various amounts of N'-(4-chloro-o-tolyl)-N,N-dimethylformamidine B. were added to establish the desired weight ratio of the two insecticides. The concentrated solutions were then diluted with water to a concentration of about 0.1% by weight of total insecticide and the solutions were applied to fields of growing cotton in the Rio Grande Valley in the requisite amount to apply predetermined amounts of active ingredients per acre.

The manner of application was by spraying in conventional manner plants whose leaves were infested with *Heliothis Viresens* and *Zea*, the cotton boll worm complex. Spraying was repeated every 3 days for a total of 6 applications in 18 days and the results determined by counting the number of live insects on the plants two days after each treatment and comparing the number with untreated plants, i.e., and effectiveness of 100% means that there were no live insects on the treated plants and 0% effectiveness means there were as many as on the untreated plants.

The results are set forth in Table 1.

TABLE 1

| Run No. | Active Ingredient | #/Acre/ Application | % effectiveness |
|---|---|---|---|
| 1 | A | 0.5 | 55.8 |
| 2 | A | 1.0 | 88.4 |
| 3 | A | 1.5 | 98.5 |
| 4 | A + B | 0.5 + 0.25 | 94.9 |
| 5 | B | 1.0 | 48.9 |

Runs 2 and 5 show that 1 pound-acre of either ingredient cannot produce a 90% kill but only 0.75 pound of the blend considerably exceeds that level of kill.

EXAMPLE 2

*Heliothis Virescens* and *Zea* (cotton boll worm complex)

Solvent: xylene
Emulsifier: alkylaryl polyglycol ether

To produce a suitable preparation of active material, a solution was made up containing 66.2 weight percent of O-ethyl-O-[4-(methylthio)phenyl]-S-propyl phosphorodithioate (A), 10 weight percent of emulsifier and 23.8 weight percent of solvent. To this solution in some instances various amounts of N'-(4-chloro-o-tolyl)-N,N-dimethylformamidine B. were added to establish the desired weight ratio of the two insecticides. The concentrated solutions were then diluted with water to a concentration of about 0.1% by weight of total insecticide and the solutions were applied to fields of growing cotton to the Rio Grande Valley in the requisite amount to apply predetermined amounts of active ingredients per acre.

The manner of application was by spraying in conventional manner plants whose leaves were infested with *Heliothis Viresens* and *Zea*, the cotton boll worm complex. Spraying was repeated every 3-6 days for a total of 11 applications over 46 days and the results determined by counting the number of live insects on the plants two days after each treatment and comparing the number with untreated plants, i.e., an effectiveness of 100% means that there were no live insects on the treated plants and 0% effectiveness means there were as many as on the untreated plants.

The results are set forth in Table 2.

TABLE 2

| Run No. | Active Ingredient | #/Acre/ Application | % effectiveness |
|---|---|---|---|
| 6 | A | 0.25 | 34.9 |
| 7 | A | 0.5 | 71.6 |
| 8 | A | 0.75 | 78.1 |
| 9 | A | 1.0 | 98.1 |
| 10 | A + B | 0.5 + 0.25 | 92.8 |
| 11 | A + B | 0.25 + 0.125 | 63.0 |

This table shows that a small amount of N'-(4-chloro-o-tolyl)-N,N-dimethylformamidine in Run 11 produces a marked increase in the effectiveness level compared with Run 6. Run 7 vs. Run 10 are to the same effect. It is noted that the level of kill in Run 10 could not be achieved in Run 9 even with considerably more total insecticide.

EXAMPLE 3

Example 2 was repeated with a total of 8 applications over 45 days, except that the xylene solution was applied without water dilution using the ultra low volume technique. The results are set forth in Table 3.

TABLE 3

| Run No. | Active Ingredient | #/Acre/ Application | % effectiveness |
|---|---|---|---|
| 12 | A | 0.5 | 64.0 |
| 13 | A | 0.75 | 76.2 |
| 14 | A + B | 0.5 + 0.25 | 86.2 |

Since Example 1 showed that pound for pound A was more effective than B, it is surprising that Run 14, wherein some of the more active material was replaced by the same amount of the less active material, showed a greater effectiveness than Run 13.

EXAMPLE 4

The process of Example 2 was repeated for a total of 5 applications over 14 days. The results are set forth in Table 4.

TABLE 4

| Run No. | Active Ingredient | #/Acre/ Application | % effectiveness |
|---|---|---|---|
| 15 | A | 0.5 | 49.6 |
| 16 | A | 1.0 | 72.8 |
| 17 | A + B | 0.5 + 0.25 | 71.5 |

Run 17 shows substantially the same effectiveness as Run 16 at only ¾ as much total insecticide, i.e., even though 0.5 pound/acre of the more active insecticide has been replaced by 0.25 pound/acre of the less active insecticide.

EXAMPLE 5

The process of Example 2 was repeated at another location with 8 applications over 34 days. The results are set forth in Table 5.

TABLE 5

| Run No. | Active Ingredient | #/Acre/ Application | % effectiveness |
|---|---|---|---|
| 18 | A | 0.5 | 92 |
| 19 | A | 0.75 | 97 |
| 20 | A | 1.0 | 98 |
| 21 | A | 1.5 | 99 |
| 22 | A + B | 1.0 + 0.25 | 97 |
| 23 | A + B | 1.0 + 0.25 | 97 |
| 24 | A + B | 0.75 + 0.25 | 97 |

These results show that this particular infestation was comparatively mild and the insects were particularly susceptible since even at the lowest levels of application the effectiveness exceeded 90%. These results, because of their closeness to one another, teach little except they certainly show there is no antagonistic effect between the two insecticides.

EXAMPLE 6

Authonomus grandis (boll weevil)

Solvent: xylene
Emulsifier: alkylaryl polyglycol ether

To produce a suitable preparation of active material, a solution was made up containing 66.2 weight precent of O-ethyl-O-[-4-(methylthio)phenyl.]-S-propyl phosphorodithioate (A), 10 weight percent of emulsifier and 23.8 weight percent of solvent. To this solution in some instances various amounts of N'(4chloro-o-tolyl-N,N-dimethylformamidine (B) were added to establish the desired weight ratio of the two insecticides. The concentrated solutions were then diluted with water to a concentration of about 0.1% by weight of total insecticides and the solutions were applied to fields of growing cotton in the Rio Grande Valley in the requisite amount to apply predetermined amounts of active ingredients per acre.

The manner of applications was by spraying in conventional manner plants whose squares were infested with Anthonomus grandis (Boll Weevil). Spraying was repeated every 3 days for a total of 6 applications over 18 days and the results determined by counting the number of live insects on the squares two days after each treatment and comparing the number with untreated plants, i.e., an effectiveness of 100% means that there were no live insects on the treated plants and 0% effectiveness means there were as many as on the untreated plants. The results were as follows:

TABLE 6

| Run No. | Active Ingredient | Application Rate Ounces Active Ingredient /Acre | % effectiveness |
|---|---|---|---|
| 25 | A | 24 | 66.5 |
| 26 | A | 16 | 62.8 |
| 27 | A | 8 | 21.8 |
| 28 | B | 16 | 0 |
| 29 | A + B | 8 + 4 | 62.3 |

EXAMPLE 7

Bucculatrix thurberiella (cotton leaf perforator)

Solvent: xylene
Emulsifier: alkylaryl polyglycol ether

To produce a suitable preparation of active material, a solution was made up containing 66.2 weight percent of O-ethyl-O-[-4-(methylthio)phenyl.]-S-propyl phosphorodithioate (A), 10 weight percent of emulsifier and 23.8 weight percent of solvent. To this solution in some instances various amounts of N-(4-chloro-o-tolyl)-N,N-dimethylformamidine (B) were added to establish the desired weight ratio of the two insecticides. The concentrated solutions were then diluted with water to a concentration of about 0.1% by weight of total insecticides and the solutions were applied to fields of growing cotton in the Rio Grande Valley in the requisite amount to apply predetermined amounts of active ingredients per acre.

The manner of applications was by spraying in conventional manner plants whose leaves were infested with Bucculatrix thurberiella. Spraying was repeated every 3 – 6 days for a total of 11 applications over 46 days and the results dtermined by counting the number of live insects on the plants two days after each treatment and comparing the number with untreated plants, i.e., an effectiveness of 100% means that there were no live insects on the treated plants and 0% effectiveness means there were as many as on the untreated plants.

TABLE 7

| Run No. | Active Ingredient | Application Rate Ounces Active Ingredient/Acre | % effectiveness |
|---|---|---|---|
| 30 | A | 4 | 60 |
| 31 | A | 8 | 50.5 |
| 32 | A | 12 | 69.5 |
| 33 | A | 16 | 81.5 |
| 34 | A + B | 8 + 4 | 94.5 |
| 35 | Methylparathion | 24 | 81.0 |
| 36 | Methylparathion + B | 24 + 4 | 56.5 |

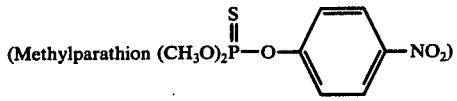

(Methylparathion $(CH_3O)_2\overset{S}{\underset{\|}{P}}-O-\underset{}{\bigcirc}-NO_2$)

Runs 35 and 36 demonstrate that compound B lowers the effect of methylparathion whereas together with compound A it shows a strong synergistic effect.

EXAMPLE 8

The process of Example 2 was repeated with 9 applications over 34 days. The results were as follows:

TABLE 8

| Run No. | Active Ingredient | #/Acre/ Application | % effectiveness |
|---|---|---|---|
| 37 | A | 0.25 | 88 |
| 38 | A | 0.5 | 91 |
| 39 | A | 0.75 | 95 |
| 40 | A | 1.0 | 95.5 |
| 41 | A | 1.5 | 98 |
| 42 | B | 0.25 | 74 |
| 43 | B | 1.5 | 86.5 |
| 44 | A + B | 0.25 + 0.25 | 86 |
| 45 | A + B | 0.5 + 0.5 | 92.5 |

The results of this test are anomalous since N'-(4-chloro-O-tolyl)-N,N-dimethylformamidine alone in Run 42, for example, was far more effective than four times the quantity in Run 11 of Example 2. Also the kills in Runs 44 and 45 are about the same as in Runs 37 and 38 which had the same amount of the first ingredient but no second ingredient. While the results show no antagonism between the two ingredients, they are otherwise inconclusive.

It will be appreciated that the instant specification and examples are set forth by way of illustration and not limitation, and that various modifications and changes may be made without departing from the spirit and scope of the present invention.

What is claimed is

1. A synergistic insecticidal composition comprising an insecticidally effective amount of O-ethyl-O-[4-(methylthio)-phenyl]-S-propyl phosphorodithioate and N'-

(4-chloro-o-tolyl)-N,N-dimethylformamidine in a weight ratio of about 1 : 0.125 – 0.5.

2. A composition according to claim 1 wherein the weight ratio is about 1 : 0.16 – 0.5.

3. A method for combating insects which comprises applying to such insects or an insect habitat an insecticidally effective amount of a composition comprising O-ethyl-O-[4-(methylthio)-phenyl]-S-propyl phosphorodithioate and N'-(4-chloro-o-tolyl)-N,N-dimethylformamidine in a weight ratio of about 1 : 0.125 – 0.5.

4. The method according to claim 3 wherein the weight ratio is about 1 : 0,16 – 0.5.

5. The method according to claim 3 wherein the composition is applied to a field in which cotton, corn, soybeans or tobacco is grown.

6. The method according to claim 3 wherein the composition is applied to a field in which cotton is grown.

7. The method according to claim 3 wherein the insect combated is of the order Lepidoptera.

8. The method according to claim 7 wherein the insect combated is of the genus Heliothis.

9. The method according to claim 8 wherein the composition is applied to a field in which cotton is grown, and the ingredients are present in a weight ratio of about 1 : 0.16 – 0.5.